(12) United States Patent
Mazanec

(10) Patent No.: US 9,313,590 B1
(45) Date of Patent: Apr. 12, 2016

(54) HEARING AID AMPLIFIER HAVING FEED FORWARD BIAS CONTROL BASED ON SIGNAL AMPLITUDE AND FREQUENCY FOR REDUCED POWER CONSUMPTION

(75) Inventor: Paul R. Mazanec, Blaine, MN (US)

(73) Assignee: ENVOY MEDICAL CORPORATION, St. Paul, MN (US)

( * ) Notice: Subject to any disclaimer, the term of this patent is extended or adjusted under 35 U.S.C. 154(b) by 336 days.

(21) Appl. No.: 13/444,464

(22) Filed: Apr. 11, 2012

(51) Int. Cl.
*H04R 25/00* (2006.01)

(52) U.S. Cl.
CPC .............. *H04R 25/70* (2013.01); *H04R 25/305* (2013.01); *H04R 25/45* (2013.01)

(58) Field of Classification Search
USPC .................................... 381/320, 312, 313, 60
See application file for complete search history.

(56) References Cited

U.S. PATENT DOCUMENTS

| | | | |
|---|---|---|---|
| 4,425,551 A | 1/1984 | Blackmer et al. | |
| 4,792,977 A | 12/1988 | Anderson et al. | |
| 7,719,345 B2 | 5/2010 | Cho et al. | |
| 2007/0127753 A1* | 6/2007 | Feng et al. | 381/313 |
| 2011/0299692 A1* | 12/2011 | Rung et al. | 381/60 |
| 2012/0093344 A1* | 4/2012 | Sun et al. | 381/122 |

\* cited by examiner

*Primary Examiner* — Duc Nguyen
*Assistant Examiner* — Phan Le
(74) *Attorney, Agent, or Firm* — Seager, Tufte & Wickhem LLP

(57) ABSTRACT

A hearing aid is disclosed, which can autonomously track the bias current requirements of its output amplifier and control the current bias accordingly, resulting in less power consumption than if the bias current were delivered at a constant, worst-case level. An input signal is split into different frequency bands. A volume envelope is formed for each frequency band, which may function like an instantaneous volume level for each frequency band. The volume envelopes are weighted by frequency, with high frequencies being weighted more heavily than low frequencies. The weighted volume envelopes are used to calculate a dynamic bias current level, and a current with that level is provided to the output amplifier of the hearing aid. In some cases, the narrowband input signals for the frequency bands are amplified with respective predetermined gains, and are then combined to form a broadband output signal, which is sent to the output amplifier.

19 Claims, 5 Drawing Sheets

HEARING AID AMPLIFIER HAVING FEED FORWARD BIAS CONTROL BASED ON SIGNAL AMPLITUDE AND FREQUENCY FOR REDUCED POWER CONSUMPTION

TECHNICAL FIELD

The present invention pertains to hearing aids, and methods for manufacturing and using such hearing aids.

BACKGROUND

Hearing restoration or compensation devices, commonly known as hearing aids, provide a tremendous benefit to a patient with congenital hearing loss or whose hearing has deteriorated due to age, genetics, illness, or injury. There is a wide variety of commercially available devices that can be worn externally or can be implanted within the body of the patient.

The service life of an implantable medical device is often limited by the battery capacity of its internal battery. In order to increase the service of the device, the electronics in the device may be designed to reduce or minimize power consumption. For hearing aids, the output amplifier or amplifiers may consume a significant portion of the overall power dissipated in the device. There is ongoing effort to develop techniques that reduce power consumption by the output amplifier.

It is desirable for a hearing aid output amplifier to retain its linearity over the full range of normal human hearing, which is typically 20 Hz to 20 kHz, and over the full dynamic range, which can typically span 60 to 80 dB. Retaining linearity is most challenging for loud signals at high frequencies. In particular, it is desirable to avoid a condition referred to as "slew rate limiting".

The slew rate at a particular point in a circuit describes how quickly the voltage must change with respect to time. One may think of a simple sine wave as an example, where the zero-crossing (being the point at which the voltage changes most quickly) places a particular requirement on the voltage change per time. As the sine wave amplitude increases, so does the slope at the zero crossing. Likewise, as the frequency of the sine wave increases, so does the slope at the zero crossing. The voltage-per-time requirements are most demanding when the sine wave simultaneously has a large amplitude and a high frequency.

Mathematically, the slew rate, or voltage change per time, requirements are linearly proportional to a current specification on the output amplifier. In other words, if the output amplifier can deliver a particular value of current, then the amplifier can provide the required voltage change per time at the most demanding conditions, which are loud volumes at high frequencies. This particular value of current is known as a "bias current".

When power dissipation is not an issue, such as for guitar amplifiers or other devices that may be plugged into a wall, the bias current may be run at a constant value. However, running the bias current at a constant value is generally unacceptable in a hearing aid or other low-power electronic devices. Such a constant-valued current would consume electrical power even when it is not required, since there are many occasions when there are not loud volumes at high frequencies.

In addition, there is a condition known as "crossover distortion". Basically, at voltages near a point where current is switched between a set of matched transistors, a kink may appear in the output voltage, which can lead to a "flattening out" of voltage at a zero crossing or at some other voltage level. Often, one can reduce or eliminate crossover distortion by increasing a bias current. Along with slew rate limiting, it is desirable to avoid crossover distortion.

Accordingly, there exists a need for a technique of delivering a required bias current to the output amplifier in a hearing aid, while consuming less hearing aid battery energy than a constant-level bias current would consume. Such a technique may also be used in other applications that use broadband amplifiers.

BRIEF SUMMARY

An embodiment is a method that includes the following steps. A broadband input signal is generated in response to ambient sound from around a patient. The broadband input signal is split into a plurality of narrowband input signals, where each narrowband input signal corresponds to a band of frequencies within the frequency range of normal human hearing. A plurality of predetermined gains are applied to the plurality of narrowband input signals to form a plurality of narrowband output signals. The plurality of narrowband output signals are combined to form a broadband output signal. The broadband output signal is amplified or buffered with an amplifier. A plurality of narrowband volume envelopes is formed from at least one of the pluralities of narrowband input signals or narrowband output signals. A weighting is applied to the plurality of narrowband volume envelopes. A dynamic bias current level is formed from the weighted plurality of narrowband volume envelopes. A dynamic bias current is applied at the dynamic bias current level to the amplifier.

Another embodiment is a hearing aid, including the following: A sensor receives ambient sound from around a patient and produces a broadband input signal in response to the ambient sound. A splitter directs portions of the broadband input signal to a plurality of narrowband amplifiers. Each narrowband amplifier receives a respective band of frequencies within the frequency range of normal human hearing. Each narrowband amplifier applies a predetermined gain to the respective narrowband input signal to form a respective narrowband output signal. A combiner combines the plurality of narrowband output signals to form a broadband output signal. A broadband amplifier amplifies the broadband output signal. The amplified broadband output signal is capable of driving a transducer that stimulates the anatomy of the patient. A plurality of monitors form a respective plurality of narrowband volume envelopes from the plurality of narrowband output signals. A bias generator receives the plurality of narrowband volume envelopes, applies a predetermined weighting to the plurality of narrowband volume envelopes, determines a dynamic bias current level from the weighted plurality of narrowband volume envelopes; and applies a dynamic bias current at the dynamic bias current level to the amplifier.

A further embodiment is a method that includes the following steps. A broadband signal is provided. The broadband signal is split into a plurality of narrowband signals. Each narrowband signal has a corresponding frequency band. A volume envelope is formed for each narrowband signal. The volume envelopes are weighted by frequency, where higher frequencies are weighted more heavily than lower frequencies. A dynamic bias current level is calculated based on the weighted volume envelopes. A dynamic bias current having the dynamic bias current level is provided to an output amplifier. The broadband signal is amplified with the output amplifier.

The above summary of some embodiments is not intended to describe each disclosed embodiment or every implementation of the present invention. The Figures and Detailed Description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
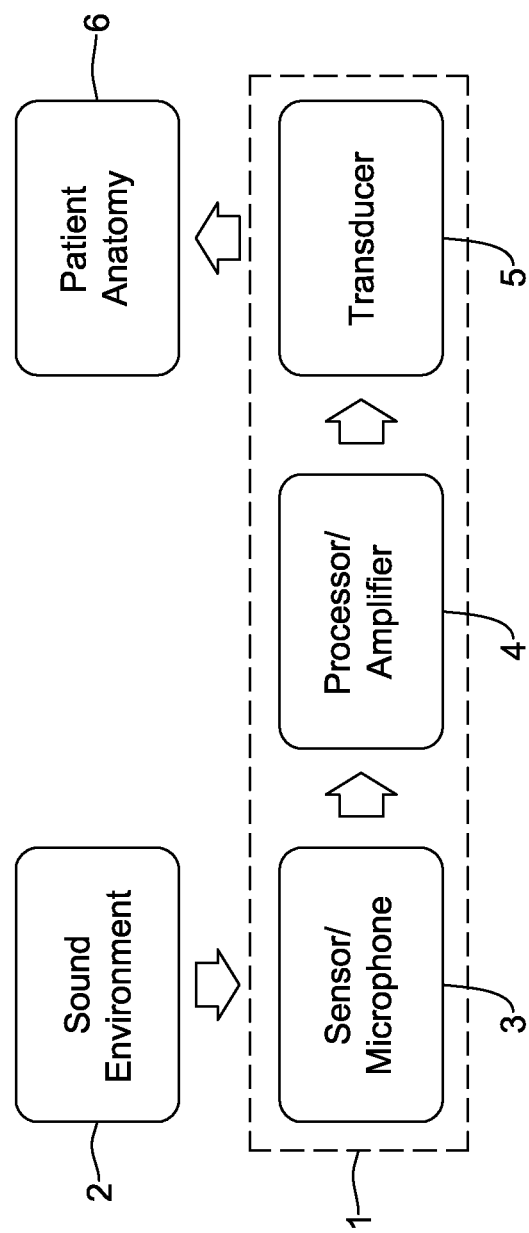
FIG. 1 is a block diagram of an implantable hearing restoration device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the purposes of this document, the term "hearing aid" is intended to mean any instrument or device designed for or represented as aiding, improving or compensating for defective human hearing and any parts, attachments or accessories of such an instrument or device.

A hearing aid is disclosed, which can autonomously track the bias current requirements of its output amplifier and control the current bias accordingly, thereby resulting in less power consumption than if the bias current were delivered at a constant, worst-case level. An input signal is split into different frequency bands. A volume envelope is formed for each frequency band, which may function like an instantaneous volume level for each frequency band. The volume envelopes are weighted by frequency, with high frequencies being weighted more heavily than low frequencies. The weighted volume envelopes are used to calculate a dynamic bias current level, and a current with that level is provided to the output amplifier of the hearing aid. In some cases, the narrowband input signals for the frequency bands are amplified with respective predetermined gains, and are then combined to form a broadband output signal, which is sent to the output amplifier.

The above paragraph is merely a general summary, and should not be construed as limiting in any way. More detail is provided in the figures and in the text that follows.

FIG. 1 is a block diagram of an implantable hearing restoration device 1, with arrows that trace the flow of acoustic signals. The acoustic signals flow from a sound environment 2, to an implantable hearing restoration device 1, to a patient anatomy 6.

The sound environment 2 may be the acoustic environment in which the patient and hearing device 1 exist, such as a quiet office, a busy street, or a soundproof booth that may be used for audiometric testing. The sound environment 2 may create sounds that are within the typical pressure and frequency range that a human with normal hearing can perceive. In general, a typical frequency range for normal human hearing may be between 20 Hz and 20 kHz, although the high-frequency edge of this range typically decreases with age. Note that the sound environment 2 may produce acoustic signals outside the frequency range of human hearing as well, although the implantable hearing restoration device 1 may be largely unaffected by these signals. Sounds produced by the sound environment 2 arrive at the implantable hearing restoration device 1 in the form of acoustic pressure waves.

The implantable hearing restoration device 1 may include three general units, including a sensor 3 or microphone 3, a processor 4 or amplifier 4, and a transducer 5. Note that the transducer 5 may also be referred to as a driver, an electrode or a speaker. For the purposes of clarity in this document, we avoid the use of the term "driver" when discussing the stimulating transducer 5, because of possible confusion with any signals that may be used as input to the processor/amplifier 4, which may be referred to as "driver" signals.

The sensor 3 may be an element or transducer that converts acoustic or mechanical energy into an electrical signal, such as a microphone. The sensor 3 receives the sound produced by the sound environment 2 and converts it into an input electrical signal. For the purposes of this document, it is assumed that the input electrical signal may be generated in a known manner.

The processor 4 processes the input electrical signal from the sensor 3, and may amplify, filter and/or apply other linear and/or non-linear algorithms to the input electrical signal. The processor 4 produces an output electrical signal and sends it to the transducer 5. In general, much of the remainder of this document is directed to particular processing performed by the processor 4, and there is much more detail concerning the processor 4 in the text that follows.

The transducer 5 receives the output electrical signal from the processor 4 and converts it into a stimulation signal that can be received by the patient anatomy 6. Depending on the type of implantable hearing restoration device 1, such as a cochlear implant or middle ear device, the stimulation signal may be acoustic, mechanical and/or electrical in nature. For the purposes of this document, it is assumed that the stimulation signal may be received in a known manner.

Figure 2:
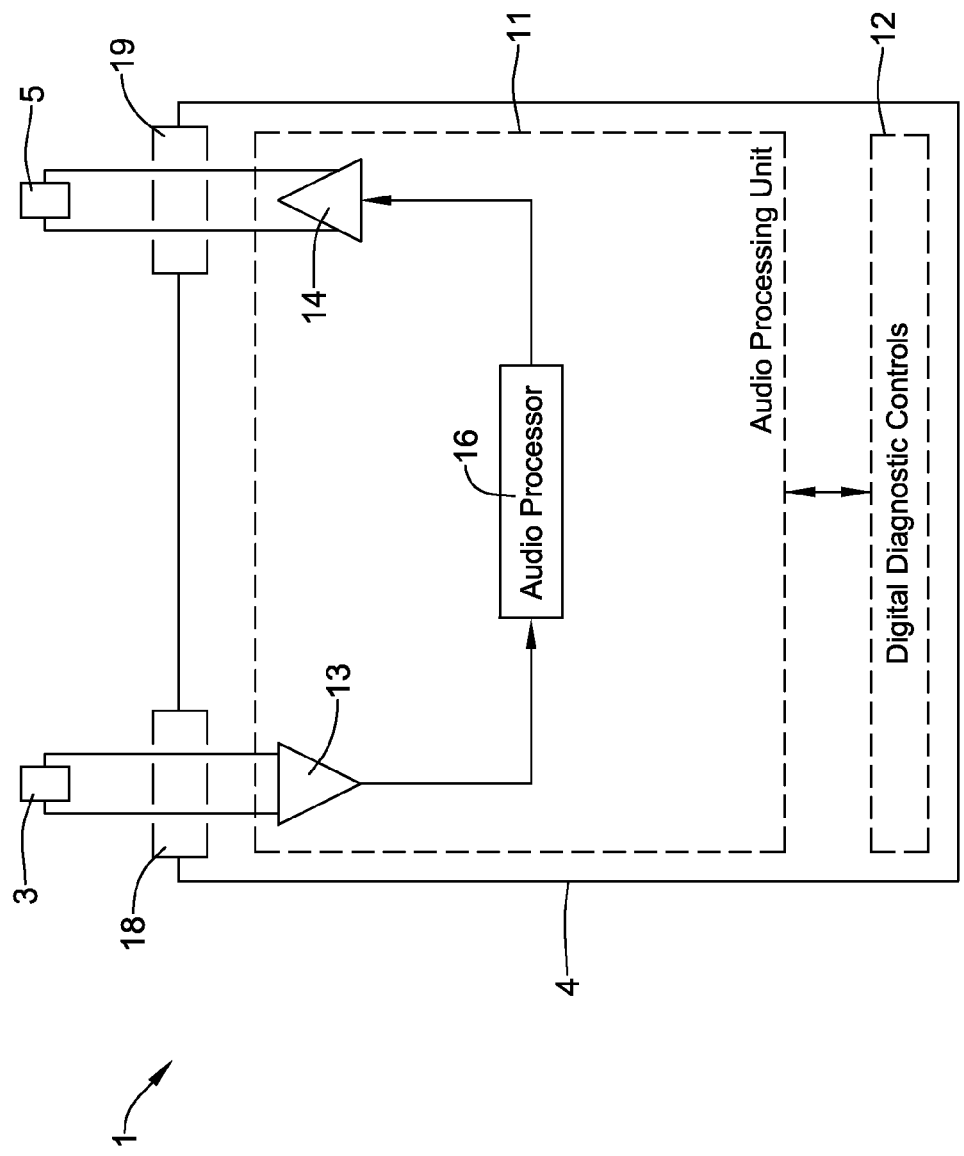
FIG. 2 is a schematic drawing of a sample implantable hearing restoration device.

FIG. 2 is a schematic drawing of a sample implantable hearing restoration device 1. In particular, the sample device 1 shows particular modules and elements that perform particular functions; it will be understood by one of ordinary skill in the art that the configuration of FIG. 2 is merely an example, and that other modules and elements may be used to perform the particular functions noted in detail below. In addition, although both the sensor 3 and the transducer 5 are shown in the example of FIG. 2 as being electrically piezoelectric in nature, it will be understood that other sensors and drivers may be used that need not be based on capacitance.

This paragraph describes the elements and components used in the day-to-day operation of the device 1. The sensor 3 electrically connects to the processor 4 through a transducer connection 18. The electrical signal produced by the sensor 3 enters an input amplifier 13. During normal use, the signal from the input amplifier 13 enters an audio processor 16, the signal from the audio processor 16 feeds an output amplifier 14, which in turn connects electrically through a transducer connection 19 to the transducer 5. Note that the day-to-day operation of the device 1 may use all-analog processing of the sound, rather than conversion to digital, processing in the digital domain, and conversion back to analog. The input amplifier 13, the audio processor 16 and the output amplifier 14 may be grouped collectively as an audio processing unit 11, although the individual components need not be physically grouped together in the same location on a circuit board or integrated circuit. The processor 4 includes a set of digital diagnostic controls 12 that can control the analog elements, and can control properties such as the gain, equalization, compression/limiting, and so forth.

As noted above, it is generally preferable to make the device 1 as energy-efficient as possible, so that batteries in the device 1 may last longer, and so that inconvenience to the patient may be reduced.

One area that may provide an increase in energy efficiency is the bias current that is supplied to the output amplifier 14. As noted above, a worst-case scenario for output power consumption, where sound simultaneously has a loud volume and a high frequency, places a particular constraint on the minimum amount of power that must be supplied to the output amplifier 14 in order to ensure that the response is linear and is relatively free from distortion. If the bias current fed to the output amplifier 14 exceeds this particular threshold, then the output from the output amplifier 14 may remain linear and distortion-free, even in the worst-case scenario of simultaneous loud volume and high frequency.

One solution is to use a constant bias current at or above the particular constraint given by the worst-case scenario. While the audio performance from the constant-level bias current may be good, the power consumed by such a constant, high-level current, may be relatively high. Such a high power draw may prematurely drain the batteries in the device 1, leading to an inconvenience for the patient.

A better solution may be to dynamically adjust the bias current in response to various properties of the incoming audio signal. For instance, if the volume of the audio is relatively low, then the output amplifier 14 may require less bias current to maintain its linear and distortion-free performance. Similarly, if the incoming audio includes relatively little high-frequency content, then the output amplifier 14 may require less bias current to maintain its linear and distortion-free performance. It is desirable to reduce the bias current when possible, while still maintaining a bias current that is large enough to satisfy the linearity and distortion-free conditions dictated by the incoming audio.

Basically, a possible technique for reducing the bias current as needed involves breaking the incoming audio into various frequency bands, extracting a volume envelope from each of the frequency bands, recombining the audio from the frequency bands (optionally with predetermined gains applied for the frequency bands that can partially compensate for any frequency dependence in the hearing loss of the patient), and amplifying the frequency-combined audio with the output amplifier. A bias controller or bias generator receives the volume envelopes, each of which may provide a volume level for the respective frequency band. The bias generator may apply a weighting based on frequency, so that the high frequencies are weighted more heavily than the low frequencies. The bias generator may determine a dynamic bias current, and may feed such a current to the output amplifier.

Figure 3:
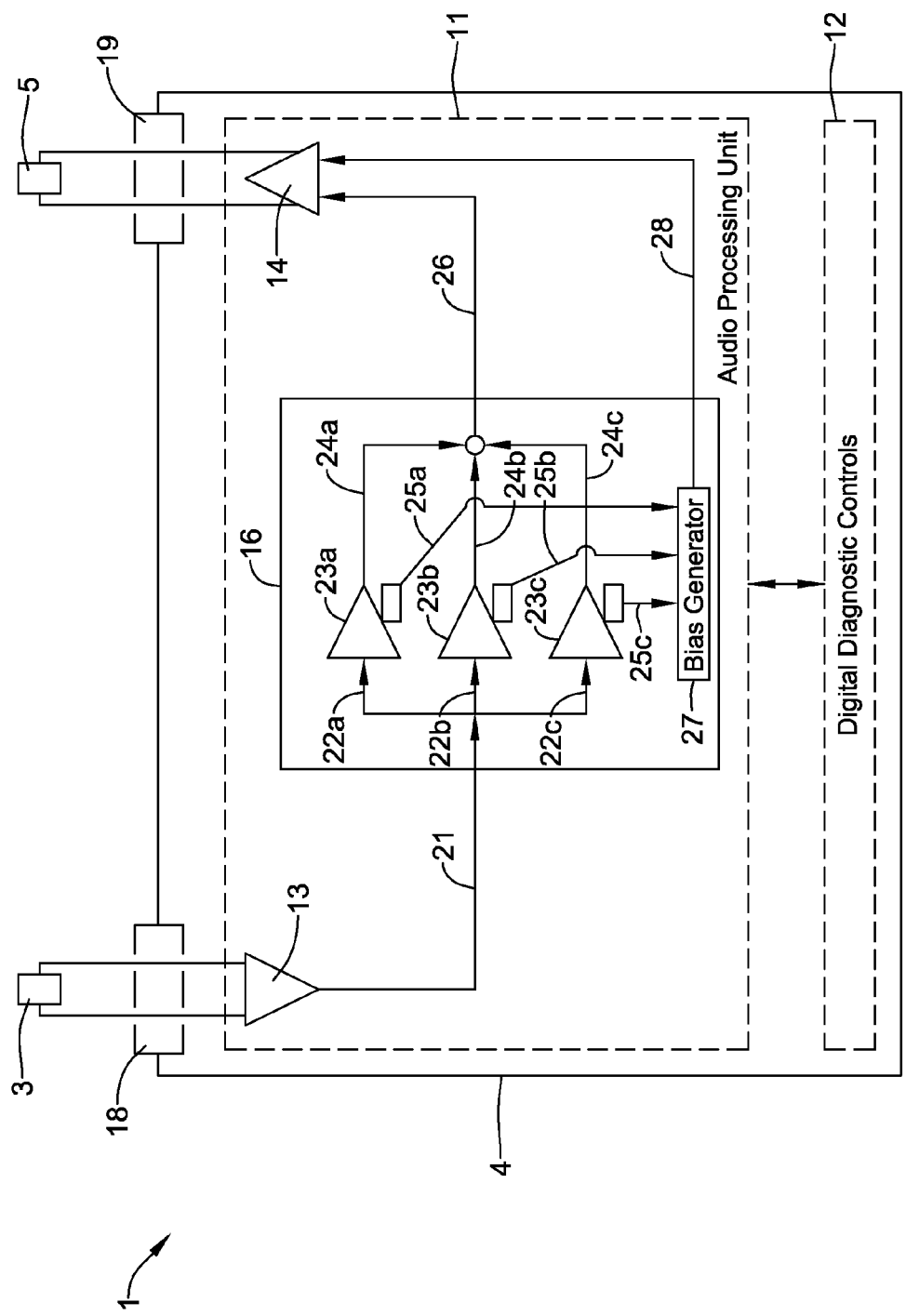
FIG. 3 is a schematic drawing of a sample implantable hearing restoration device including a dynamic bias control generator.

FIG. 3 is a schematic drawing of a sample implantable hearing restoration device 1 having an audio processor 16 that can deliver a dynamic bias current to the output amplifier 14. The audio processor 16 receives a broadband input signal 21 from the input amplifier 13, which is in response to ambient sound from around the patient.

The broadband input signal 21 is then split into a plurality of narrowband input signals 22a, 22b, 22c and so forth. Although there are only three narrowband paths shown in FIG. 3, it will be understood that more or fewer than three paths may also be used. The narrowband paths may each cover a different part of the full frequency range of normal human hearing, which is typically between 20 Hz and 20 kHz. The splitting may be accomplished by a dedicated element that includes various notch or edge filters, and/or may involve separate notch or edge filters on each of the various signal paths. In some cases, the narrowband paths subtend the full frequency range of normal human hearing. In other cases, the narrowband paths subtend only a portion of the full frequency range of normal human hearing. The frequency ranges of the narrowband paths may or may not overlap.

The narrowband input signals 22a, 22b, 22c are directed to respective narrowband amplifiers 23a, 23b, 23c. In some cases, the narrowband amplifiers 23a, 23b, 23c are used to help correct for any spectral nonuniformities in the hearing loss of the patient. For these cases, each narrowband amplifier 23a, 23b, 23c applied a predetermined gain to the respective narrowband input signal 22a, 22b, 22c, where the predetermined gains may be determined beforehand by a clinician when installing the hearing aid. The narrowband amplifiers 23a, 23b, 23c have respective narrowband outputs 24a, 24b, 24c, which may be combined into a single broadband output signal 26 that is fed to the output amplifier 14.

The narrowband amplifier 23a, 23b, 23c may include respective monitors that generate respective volume envelopes 25a, 25b, 25c. The volume envelopes 25a, 25b, 25c may be formed as a time-average of a respective narrowband output signal 24a, 24b, 24c, where the time-average may be taken over a time window of a suitable length. The volume envelopes 25a, 25b, 25c may effectively provide near-instantaneous volume levels for the respective narrowband output signals 24a, 24b, 24c.

The volume envelopes 25a, 25b, 25c are received by a bias generator 27. The bias generator 27 may apply a weighting to the volume envelopes 25a, 25b, 25c to reflect the influence of frequency on the required bias current. For instance, high frequencies may be weighted more heavily than low frequencies. Based on the weighted volume envelopes 25a, 25b, 25c, the bias generator arrives at a dynamic bias current level, and applies a dynamic bias current 28 at the dynamic bias current level to the output amplifier 14. Because the dynamic bias current level varies with the volume envelopes 25a, 25b, 25c, the bias current level may be lowered when the ambient sound is relatively quiet and/or does not include loud, high-frequency sounds. Reducing the bias current, when possible, reduces the amount of energy consumed by the device 1, thereby increasing the battery life and reducing the inconvenience to the patient.

In some cases, the bias generator 27 may calculate the dynamic bias current level, based in part on the received volume envelopes 25a, 25b, 25c and the predetermined weighting for each frequency band. In other cases, the bias generator 27 may use a lookup table to determine the dynamic bias current level, based in part on the received volume envelopes 25a, 25b, 25c and the predetermined weighting for each frequency band.

In some cases, there may not be any gain applied to each narrowband signal. For these cases, the narrowband input and narrowband output signals may be the same, with a monitor in each frequency band to determine a volume envelope from the respective narrowband input/output signal. For these cases, there is no alteration of relative gains of the frequency bands between the splitting and recombining, so that the recombined signal may closely resemble the pre-split signal.

In most cases, the volume envelopes 25a, 25b, 25c are determined for the narrowband output signals 24a, 24b, 24c, since those are the signals that are combined and are sent to the output amplifier 14. In some cases, the volume envelopes 25a, 25b, 25c may be determined from the narrowband input signals 22a, 22b, 22c, rather than the narrowband output signals 24a, 24b, 24c.

The dynamic bias current may be updated or refreshed periodically with a predetermined period between refreshes. Alternatively, the dynamic bias current may be updated or refreshed intermittently as needed, such as whenever the current level crosses a predetermined threshold or increases by a predetermined increment over a given value.

Figure 4:
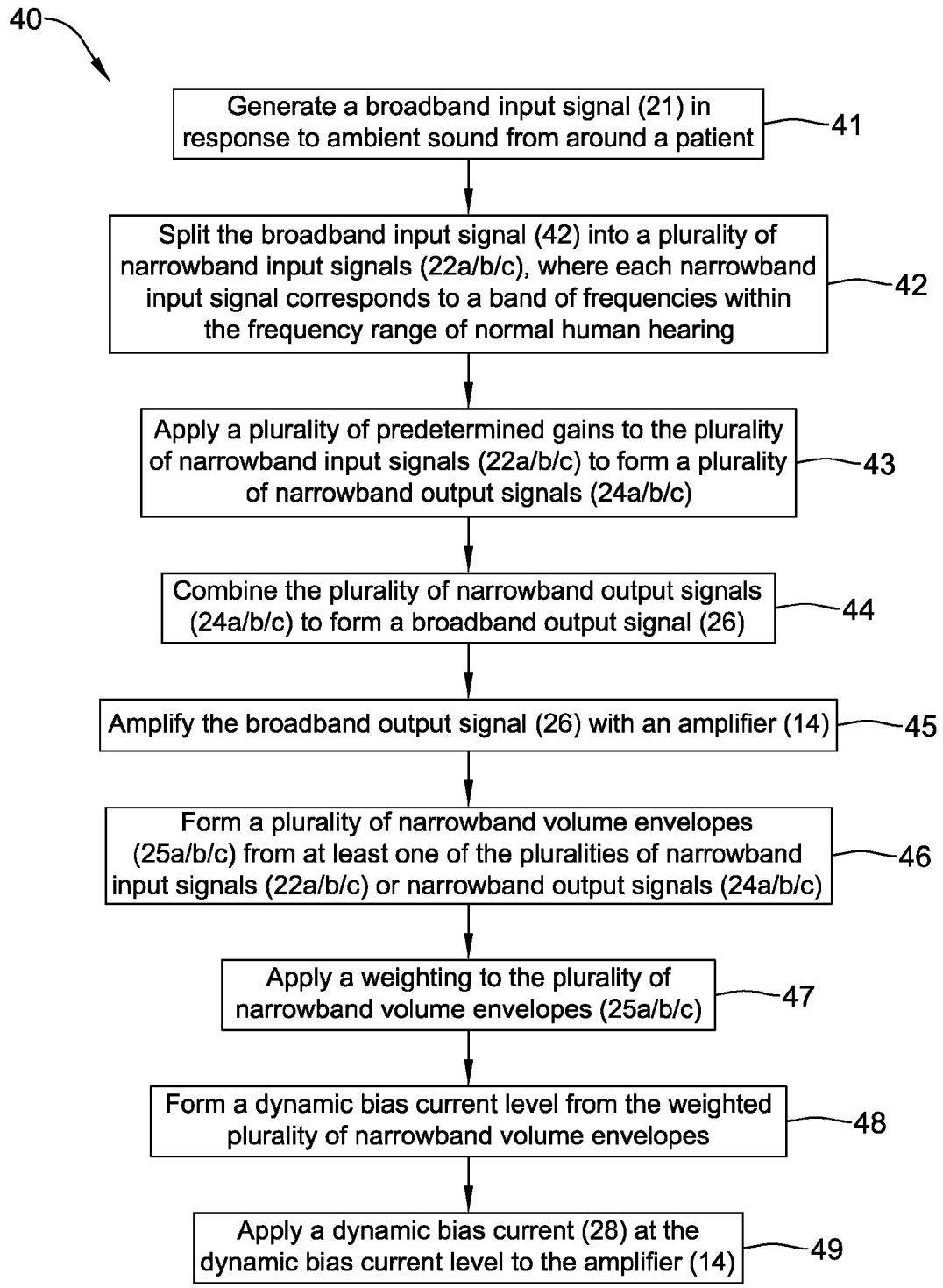
FIG. 4 is a sample flow chart of operation for the device of FIGS. 1-3.
Figure 5:
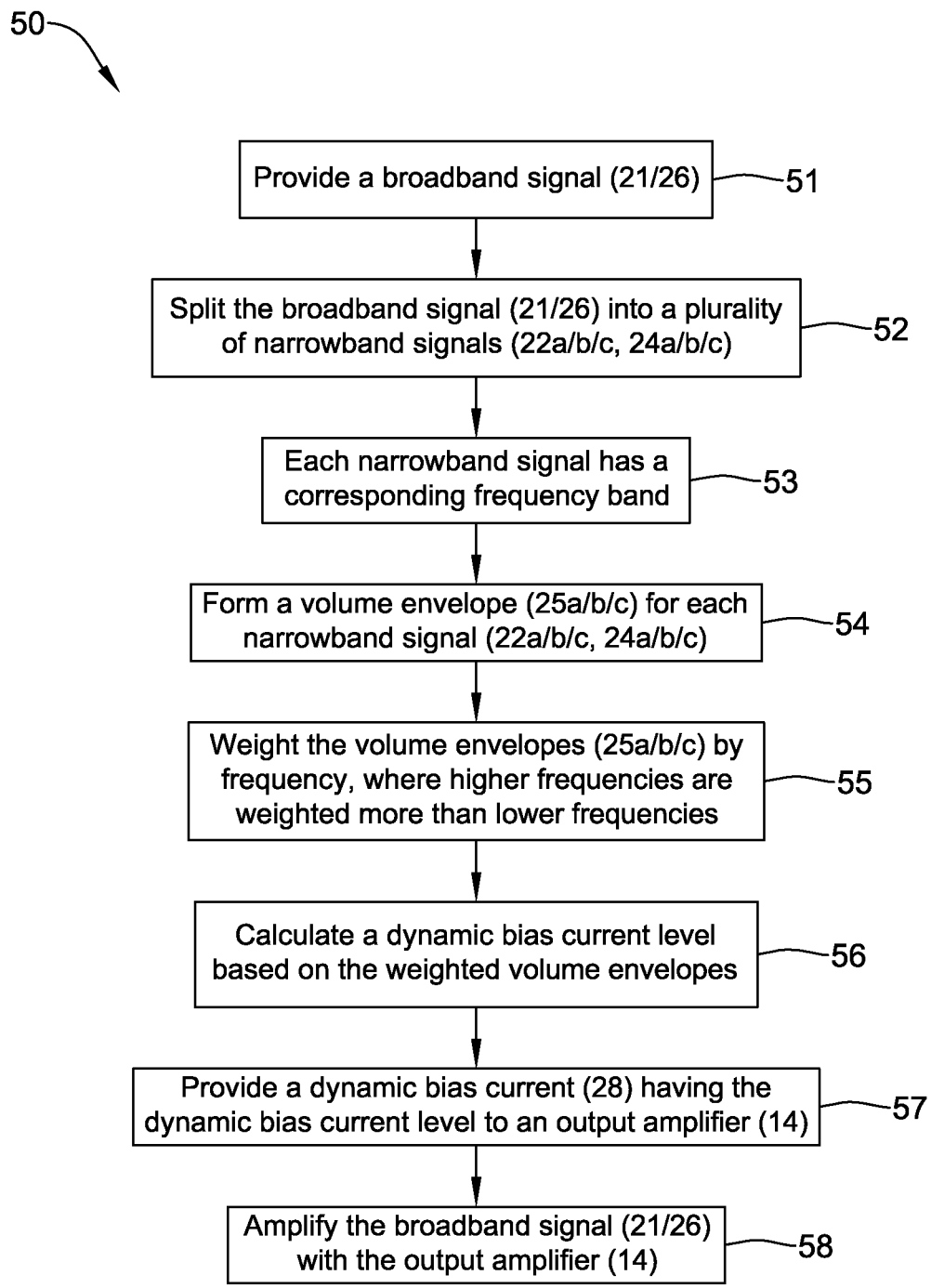
FIG. 5 is another sample flow chart of operation for the device of FIGS. 1-3.

Two methods of operation may be summarized in the flow charts of FIGS. 4 and 5.

In FIG. 4, method 40 includes the following steps. In step 41, a broadband input signal 21 is generated in response to ambient sound from around a patient. In step 42, the broadband input signal 21 is split into a plurality of narrowband input signals 22a, 22b, 22c, where each narrowband input signal 22a, 22b, 22c corresponds to a band of frequencies within the frequency range of normal human hearing. In step 43, a plurality of predetermined gains are applied to the plurality of narrowband input signals 22a, 22b, 22c to form a plurality of narrowband output signals 24a, 24b, 24c. In step 44, the plurality of narrowband output signals 24a, 24b, 24c are combined to form a broadband output signal 26. In step 45, the broadband output signal 26 is amplified with an amplifier 14. In step 46, a plurality of narrowband volume envelopes 25a, 25b, 25c is formed from at least one of the pluralities of narrowband input signals 22a, 22b, 22c or narrowband output signals 24a, 24b, 24c. In step 47, a weighting is applied to the plurality of narrowband volume envelopes 25a, 25b, 25c. In step 48, a dynamic bias current level is formed from the weighted plurality of narrowband volume envelopes 25a, 25b, 25c. In step 49, a dynamic bias current 28 is applied at the dynamic bias current level to the amplifier 14. Note that step 45 may alternatively follow 49, instead of being between steps 44 and 46. In practice, many of these steps occur in parallel, and the precise sequence of steps shown in FIG. 4 may be secondary.

In FIG. 5, method 50 includes the following steps. In step 51, a broadband signal 21/26 is provided. In step 52, the broadband signal 21/26 is split into a plurality of narrowband signals 22a, 22b, 22c, 24a, 24b, 24c. In step 53, each narrowband signal 22a, 22b, 22c, 24a, 24b, 24c has a corresponding frequency band. In step 54, a volume envelope 25a, 25b, 25c is formed for each narrowband signal 22a, 22b, 22c, 24a, 24b, 24c. In step 55, the volume envelopes 25a, 25b, 25c are weighted by frequency, where higher frequencies are weighted more heavily than lower frequencies. In step 56, a dynamic bias current level is calculated based on the weighted volume envelopes. In step 57, a dynamic bias current 28 having the dynamic bias current level is provided to an output amplifier 14. In step 58, the broadband signal 21/26 is amplified with the output amplifier 14.

Note that the notation of "21/26" is intended to cover two possibilities: (1) that the narrowband signals are recombined with a particular weighting for each band, as is shown explicitly in FIG. 3, and (2) that the particular weighting for each band may be unity or may be the same for all bands. In case (2), the un-weighted bands are recombined, so that signal 26 resembles signal 21, possibly with a change in gain if all the weightings are equal and are not unity. For case (2), this is functionally equivalent to sending the broadband input directly to the output amplifier, and using the splitting into bands only for generation of the bias signal. It is intended that FIG. 3 also covers case (2) as a special case where all the gains from amplifiers 23a/b/c are all unity.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a," "an," and "the" include plural referents unless the content clearly dictates otherwise. As used in this specification and the appended claims, the term "or" is generally employed in its sense including "and/or" unless the content clearly dictates otherwise.

The preceding detailed description should be read with reference to the drawings in which similar elements in different drawings are numbered the same. The drawings, which are not necessarily to scale, depict illustrative embodiments and are not intended to limit the scope of the invention.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method, comprising:
   generating a single broadband input signal in response to ambient sound from around a patient;
   splitting the broadband input signal into a plurality of narrowband input signals, each narrowband input signal corresponding to a band of frequencies within the frequency range of normal human hearing,
   wherein the bands of frequencies corresponding to the plurality of narrowband input signals subtend the full frequency range of normal human hearing;
   applying a plurality of predetermined gains to the plurality of narrowband input signals to form a plurality of narrowband output signals;
   combining the plurality of narrowband output signals to form a broadband output signal;
   amplifying the broadband output signal with an amplifier;
   forming a plurality of narrowband volume envelopes from at least one of the pluralities of narrowband input signals or narrowband output signals;
   applying a weighting to the plurality of narrowband volume envelopes,
   forming a dynamic bias current level from the weighted plurality of narrowband volume envelopes; and
   applying a dynamic bias current at the dynamic bias current level to the amplifier.

2. The method of claim 1, wherein for the weighting for the plurality of narrowband volume envelopes, for comparable volume levels, for higher frequencies are weighted more heavily than lower frequencies.

3. The method of claim 1,
   wherein each volume envelope is formed from a time-average of a respective narrowband output signal;

whereby each volume envelope provides a near-instantaneous volume level for the respective narrowband output signal.

4. The method of claim 1, wherein as the narrowband volume envelopes increase, the dynamic bias current level increases.

5. The method of claim 1, wherein the plurality of narrowband volume envelopes is formed from the plurality of narrowband output signals.

6. The method of claim 1, further comprising:
directing the amplified broadband output signal to a transducer; and
stimulating the anatomy of the patient with the transducer.

7. The method of claim 1, wherein the dynamic bias current level is less than or equal to a maximum value, the maximum value corresponding to a predetermined highest volume at the highest frequency in the frequency range of normal hearing.

8. The method of claim 1, wherein the frequency range of normal human hearing is from 20 Hz to 20 kHz.

9. A hearing aid, comprising:
a sensor that receives ambient sound from around a patient and produces a single broadband input signal in response to the ambient sound;
a splitter that directs portions of the broadband input signal to a plurality of narrowband amplifiers, each narrowband amplifier receiving a respective band of frequencies within the frequency range of normal human hearing; each narrowband amplifier applying a predetermined gain to the respective narrowband input signal to form a respective narrowband output signal,
wherein the bands of frequencies corresponding to the plurality of narrowband input signals subtend the full frequency range of normal human hearing;
a combiner that combines the plurality of narrowband output signals to form a broadband output signal;
a broadband amplifier that amplifies the broadband output signal, the amplified broadband output signal being capable of driving a transducer that stimulates the anatomy of the patient;
a plurality of monitors that form a respective plurality of narrowband volume envelopes from the plurality of narrowband output signals;
a bias generator that receives the plurality of narrowband volume envelopes, applies a predetermined weighting to the plurality of narrowband volume envelopes, determines a dynamic bias current level from the weighted plurality of narrowband volume envelopes; and applies a dynamic bias current at the dynamic bias current level to the amplifier.

10. The hearing aid of claim 9, wherein for the weighting for the plurality of narrowband volume envelopes, for comparable volume levels, for higher frequencies are weighted more heavily than lower frequencies.

11. The hearing aid of claim 9,
wherein each volume envelope is formed from a time-average of a respective narrowband output signal;
whereby each volume envelope provides a near-instantaneous volume level for the respective narrowband output signal.

12. The hearing aid of claim 9, wherein as the narrowband volume envelopes increase, the dynamic bias current level increases.

13. The hearing aid of claim 9, wherein the bands of frequencies corresponding to the plurality of narrowband input signals subtend the full frequency range of normal human hearing.

14. The hearing aid of claim 9, wherein the dynamic bias current level is less or equal to a maximum value, the maximum value corresponding to a predetermined highest volume at the highest frequency in the frequency range of normal hearing.

15. The hearing aid of claim 9, wherein the frequency range of normal human hearing is from 20 Hz to 20 kHz.

16. A method, comprising:
providing a single broadband signal;
splitting the broadband signal into a plurality of narrowband signals, each narrowband signal having a corresponding frequency band,
wherein the bands of frequencies corresponding to the plurality of narrowband input signals subtend the full frequency range of normal human hearing;
forming a volume envelope for each narrowband signal;
weighting the volume envelopes by frequency, wherein higher frequencies are weighted more heavily than lower frequencies;
calculating a dynamic bias current level based on the weighted volume envelopes;
providing a dynamic bias current having the dynamic bias current level to an output amplifier; and
amplifying the broadband signal with the output amplifier.

17. The method of claim 16,
wherein the broadband signal is an electrical signal produced by a sensor that receives ambient sound from around a patient; and
wherein the amplified broadband signal is directed to a transducer that stimulates the anatomy of the patient.

18. The method of claim 16, further comprising:
applying a plurality of predetermined gains to the plurality of narrowband signals to form a plurality of narrowband output signals;
combining the plurality of narrowband output signals to form a broadband output signal; and
modifying the broadband signal to be the broadband output signal, so that the broadband output signal is amplified with the output amplifier.

19. The method of claim 18, wherein the plurality of predetermined gains at least partly compensates for a frequency dependence of a hearing loss of a patient.

\* \* \* \* \*